United States Patent [19]

Humphries et al.

[11] 4,444,044

[45] * Apr. 24, 1984

[54] METHOD AND APPARATUS FOR DETERMINING THE FOAMING CHARACTERISTICS OF A CRUDE OIL STREAM AT THE WELLHEAD

[75] Inventors: Curtis L. Humphries, Duncanville; Melwyn L. Mathis, Arlington; Eddie F. Schultz, Arlington; Henry A. Seal, Arlington, all of Tex.

[73] Assignee: Mobil Oil Corporation, New York, N.Y.

[*] Notice: The portion of the term of this patent subsequent to Jan. 24, 2001 has been disclaimed.

[21] Appl. No.: 399,943

[22] Filed: Jul. 20, 1982

[51] Int. Cl.³ .................... G01N 13/00; G01N 33/28
[52] U.S. Cl. .................................................. 73/60.1
[58] Field of Search ............................. 73/60.1, 61.3

[56] References Cited

U.S. PATENT DOCUMENTS

| | | | |
|---|---|---|---|
| 2,306,606 | 12/1942 | Hirsch | 73/61.3 |
| 2,662,393 | 12/1953 | Rzasa | 73/61.3 |
| 3,151,061 | 9/1964 | Orr | 73/60.1 |
| 4,018,089 | 4/1977 | Dzula et al. | 73/863.61 |

FOREIGN PATENT DOCUMENTS

| | | | |
|---|---|---|---|
| 735795 | 5/1943 | Fed. Rep. of Germany | 73/60.1 |
| 2207458 | of 1973 | Fed. Rep. of Germany | 73/60.1 |
| 277397 | of 1970 | U.S.S.R. | 73/60.1 |
| 415554 | of 1974 | U.S.S.R. | 73/60.1 |

Primary Examiner—S. Clement Swisher
Attorney, Agent, or Firm—Alexander J. McKillop; Michael G. Gilman; Lawrence O. Miller

[57] ABSTRACT

A method for determining the foaming characteristics of a crude oil stream at the wellhead comprising introducing the production crude oil stream from the wellhead into an elongated, horizontal separator under reduced pressure at a controlled flow rate, withdrawing evolved gas from the upper portion of the separator and measuring the flow rate thereof, withdrawing oil from the lower portion of the separator and measuring the flow rate thereof, controlling the pressure on the separator at a lower pressure than the wellhead pressure, controlling the liquid level of the oil in the separator, measuring the volume of oil in the separator, and measuring the volume of foam in the separator. The apparatus comprises an elongated horizontal separator, a crude oil inlet into one end of the separator, means for supplying a crude oil stream from the wellhead to the crude oil inlet in the separator at a controlled flow rate, means for controlling the pressure in the separator at a pressure lower than the wellhead pressure, means for withdrawing gas from the upper portion of the separator and measuring the flow rate thereof, means for withdrawing crude oil from the lower portion of the separator and measuring the flow rate thereof, means for controlling the liquid level crude oil in the separator, means for measuring the volume of foam formed in the separator, and means for measuring the volume of crude oil in the separator.

15 Claims, 2 Drawing Figures

METHOD AND APPARATUS FOR DETERMINING THE FOAMING CHARACTERISTICS OF A CRUDE OIL STREAM AT THE WELLHEAD

FIELD AND BACKGROUND OF THE INVENTION

1. Field of the Invention

The invention relates to a method and apparatus for determining the foaming characteristics of crude oil streams at the wellhead.

2. Background of the Invention

The foaming characteristics of crude oil streams produced from a well are important in designing apparatus for separating the crude oil stream into oil and gas. The most common method of separating oil and gas produced from a well is to pass the oil and gas mixture under an initial high pressure into a vessel under reduced pressure wherein the gases dissolved in the oil flash off the oil and the heavier oil separates from the gas by gravity. The volume of the vessel and the retention time of the oil is sufficient to allow the oil to accumulate and is withdrawn from the bottom portion of the vessel with the separated gas being withdrawn from the top portion of the vessel. As gas separates from the oil, foam accumulates on the top of the oil and the amount of foam formed will vary depending upon the characteristics of the crude oil being produced. Therefore, the capacity of the vessel must be sufficient to accommodate the volume of foam formed in the vessel based upon the foaming characteristics of the crude oil and crude oil production.

Conventionally, separators are designed on the basis of broad general experience. They commonly are sized to be larger than would be required to handle predicted production through the vessels. As a result, there is no adequate procedure for the design of separator vessels that are optimally sized for the production stream. Nor is there a good procedure for the sizing of separators for a new oil field, based on properties of oil samples taken in drill stem tests of discovery wells. As a result, significant amounts of money are wasted in the costs of off-shore platform construction, for both deck space and supportive capability, as well as in the costs of oversized vessels.

Presently, the foaming characteristics of oil are measured by bubbling a gas through a sparger tip into a given volume of oil, contained in some suitable measuring vessel. This practice is unsatisfactory because the character of the sparger tip may change over a period of usage and resulting foams are not be properly comparable. Furthermore, the bubbles of foam formed with sparger systems are usually larger than those which result from the self-nucleation of foam by decreasing the pressure on a gas-saturated liquid, i.e., when the gas is "flashed" from the liquid.

In copending application to C. L. Humphries et al filed June 18, 1982, Ser. No. 390,098, now U.S. Pat. No. 4,426,879 there is disclosed a method for measuring foaming characteristics of crude oil comprising saturating the crude oil with a gas inert to the crude oil under high pressure and passing the gas-saturated oil into a flash separator comprising a transparent elongated horizontal cylinder under reduced pressure wherein the amount of foam formed is measured with respect to the amount of gas withdrawn from the separator and the amount of oil contained therein.

The present invention is an improved method and apparatus for determining the foaming characteristics of crude oil at the wellhead comprising introducing the crude oil stream into a separator under reduced pressure and measuring the amount of foam formed based upon the amount of gas evolved and the amount of oil contained therein.

SUMMARY

The present invention relates to a method for measuring the foaming characteristics of a gaseous crude oil well stream comprising flowing the well stream from the well at a predetermined pressure, introducing the well stream at a controlled flow rate into one end of a separator comprising an elongated horizontal vessel under a controlled pressure lower than the well stream pressure so that the well stream separates into a gaseous portion that passes to the upper portion of the separator, a body of liquid oil that extends along the bottom of the separator and a layer of foam that accumulates on the top of the body of oil. The temperature of the crude oil stream entering the separator is measured. Gas is withdrawn from the upper portion of the separator near the end opposite the crude oil inlet and its flow rate and pressure are measured. Crude oil is withdrawn from the bottom portion of the separator opposite the crude oil inlet and its flow rate is measured. The liquid level of the oil in the separator is controlled. The volume of oil and foam in the separator are measured visually by means of a glass window provided in the end of the separator opposite the oil inlet. The wellhead pressure varies within the range of 100 to 700 psi and the reduced pressure within the separator is controlled within the range of 75 to 300 psi. The apparatus for measuring the foaming characteristics of a gaseous crude oil well stream flowing in a production line comprises an elongated horizontal separator, a crude oil inlet in one end of the separator, a crude oil flow conduit connecting the crude oil inlet with the crude oil production line near the wellhead, means for controlling the flow rate of the crude oil entering the separator, means for measuring the temperature of the crude oil stream entering the separator, an oil outlet line opening from the lower portion of the separator, an oil flow conduit connecting the oil outlet line with the well stream production line downstream of the crude oil flow conduit connecting the oil inlet of the separator with the production line, means for measuring the flow rate of the oil in the crude oil flow conduit communicating with the oil outlet of the separator, means for measuring the total rate of flow of the oil being withdrawn from the separator, means for controlling the liquid level of oil in the separator, a gas outlet line opening from the upper portion of the separator near the end opposite the crude oil inlet, a gas flow conduit connecting the gas outlet line with the oil flow line from the separator, back pressure control means in the gas outlet line for controlling the pressure in the separator to a predetermined level lower than the pressure of the crude oil well stream, means for measuring the pressure and flow rate of the gas in the gas flow conduit from the separator, means for measuring the volume of oil in the separator, and means for measuring the volume of foam in the separator.

DESCRIPTION OF THE PREFERRED EMBODIMENTS

Figures 1, 2:
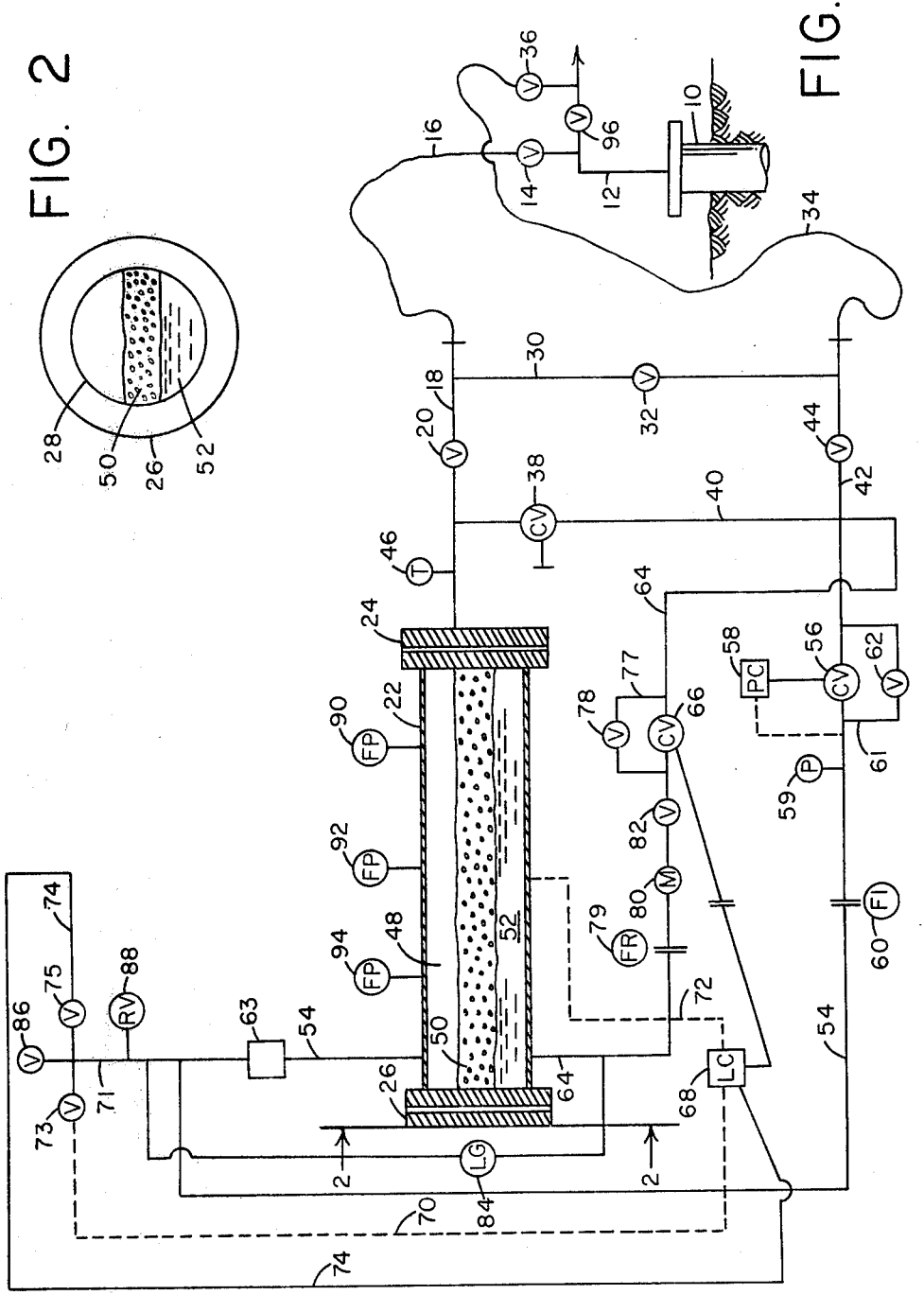
FIG. 1 is a schematic drawing of one embodiment of a system which may be employed in the practice of the invention.
FIG. 2 is a vertical end view taken upon the line 2—2 of FIG. 1.

Referring to FIG. 1, the numeral 10 designates a producing well flowing by a manifold or other suitable connection through a production line 12. The crude oil stream containing dissolved gases from well 10 is withdrawn from production line 12 via valve 14 and flexible line 16 at well head pressure. The crude oil well stream may pass into line 16 at a pressure within the range of 100 to 700 psi, depending upon the particular well being produced.

The crude oil well stream which contains dissolved gases is introduced through feed line 18 and valve 20 into an elongated horizontal separator 22 under substantially reduced pressure closed at one end by flange 24 and at the opposite end by flange 26. The center portion of flange 26 is provided with a glass window 28 for viewing the oil level and foam level in the flash separator 22, see FIG. 2. The glass window 28 is sealed with suitable gaskets to withstand a pressure of 300 psi. Temperature of the crude oil stream in line 18 is measured by a thermometer 46.

The total well stream flowing in line 18 may be bypassed back to production line 12 via branch line 30, valve 32, flexible line 34 and valve 36.

Flow through the crude oil well stream supply line 18 to the separator 22 is controlled by a normally open regulating valve 38 connected to line 18 by branch line 40. Line 42 and valve 44 are connected to line 40 for delivering the well stream passing through line 40 into production line 12 via line 34.

The crude oil well stream entering separator 22 under substantially reduced pressure separates into a gas phase 48, a liquid oil phase 52, and a layer of foam 50 that accumulates on top of the liquid oil phase. Gas is withdrawn from the separator 22 through gas outlet line 54 opening from the upper portion of the separator opposite the oil inlet end and is delivered into production line 12 via lines 42 and 34. A back pressure control valve 56 connected to a pressure control means 58 of conventional design is connected to line 54 to control the pressure within the separator 22. The pressure in separator 22 is controlled within the range of 75 psi to 300 psi. A pressure gauge 59 is connected to gas outlet line 54 for measuring the pressure of the gas therein. The gas flow rate in line 54 is measured by a suitable gas flow instrument 60 such as an orifice meter. Bypass line 61 is provided around back pressure valve 56 and in communication with gas outlet line 54. A valve 62 is provided in bypass line 61. A sight glass 63 is provided in gas outlet line 54 for observing any foam carryover with the evolved gas being withdrawn from the upper portion of the separator 22.

Oil is withdrawn from the lower portion of the flash separator through oil outlet line 64 located at the end of the separator opposite the oil inlet end and is delivered to production line 12 via lines 42 and 34. A conventional liquid level control valve 66 is operably connected to a liquid level control instrument 68 in fluid communication with the upper portion of the separator 22 by line 70 connected to gas outlet line 54 via branch line 71 and to the lower portion of the separator by line 72 located in the center portion of the separator. A ball valve 73 is provided in line 70. The liquid level control instrument 68 receives supply gas through valve 75 and line 74 and delivers it through liquid level control instrument 68 to the diaphragm of control valve 66. Control valve 66 is actuated by the liquid level in the flash separator 22 through control instrument 68 thereby controlling the level of the crude oil in the separator to the desired level. Bypass line 77 is provided around control valve 66 and in communication with oil outlet line 64. A valve 78 is provided in bypass line 77. A suitable flow recorder 79 such as an orifice meter is provided in oil outlet 64 for measuring the oil flow rate. A meter 80 is provided in oil outlet line 64 for measuring the cumulative volume of oil flowing from the separator 22. A shutoff valve 82 which is normally open is provided in oil outlet line 64.

The crude oil liquid level in flash separator 22 is visually measured by means of a conventional liquid level gauge 84 vertically mounted on the outside of the separator in fluid communication with the oil outlet line 64 and the gas outlet line 54.

A normally closed valve 86 is connected to line 71 which may be used to vent line 71. A pressure relief valve 88 is also provided in line 71.

If desired, foam probes 90, 92, and 94, equally spaced apart, are provided in the upper portion of the separator 22 to locate the height of the layer of foam 50 as described below.

OPERATION

In operation of the separator 22, a crude oil stream containing dissolved gases flowing from well 10 through production line 12 is conducted through flexible line 16, bypass line 30, and returned to the production line through flexible line 34 with valves 14, 32, and 36 opened and valves 20, 44 and 96 closed.

The crude oil stream is then introduced into separator 22 via line 18 by opening valve 20 and closing valve 32. A portion of the crude oil stream not flowing to the separator 22 is bypassed to production line 12 through line 40, 42, open valve 44, flexible line 34 and open valve 36. The rate of flow of crude oil stream directed to separator 22 through line 18 is controlled by means of control valve 38 in bypass line 40 in communication with production line 12 downstream line 16. Temperature of the crude oil entering the separator 22 via line 18 is measured by thermometer 46.

The pressure controller 58 and liquid level controller 68 are set to the desired value to maintain the desired pressure and oil level in separator 22. The body of oil 52 extends along the entire length of the separator 22 and the lighter foam accumulates in layer 50 on top of the body of oil 52. The separated gas passes upwardly into the top portion of the separator 22 and through gas outlet line 54 and is returned to production line 12 via lines 42 and 34. The pressure in separator 22 is controlled to a pressure lower than the wellhead pressure by back pressure valve 56 in gas outlet line 54 connected to pressure contoller 58.

The rate of flow of the oil withdrawn from the separator 22 via line 64 is measured by a flow indicator 79 and the cumulative volume of oil flow is measured by a meter 80.

The gas flow rate in gas outlet line 54 is measured by flow indicator 60 and the pressure is measured by pressure gauge 59.

The liquid level in separator 22 is controlled by means of control valve 66 connected to liquid level controller 68. The oil and foam levels in the separator 22 are visually measured through glass window 28 mounted in the center of outlet flange 26, see FIG. 2. If desired, the foam level may be measured by means of foam probes 90, 92, and 94 that extend into the upper portion of the separator 22. The foam probes can be used to determine the slope, if any, of the top of the foam.

The foam probes 90, 92 and 94 consist of stainless tubing with a valve attached at the upper end of the tubing and are inserted into separator 22 through a packed fitting which allows the foam probe to be raised or lowered with very little gas leakage through the packaging.

When the lower end of the foam probe is in the gas in separator 22, only clean gas will be vented when the valve at the top of the foam probe is opened. By slowly pushing the foam probe into separator 22, the top of the foam is located when oil droplets start to spew from the opened valve at the top of the foam probe.

The data from the separator 22 is used to measure the foaming characteristics of a crude oil stream subjected to flash separation as indicated by the following Example:

EXAMPLE

Data from an actual well test are as follows:

|  | Test 1 | Test 2 | Test 3 |
|---|---|---|---|
| $V_F$, cubic feet | .2523 | .2280 | .3003 |
| $V_o$, barrels | .1960 | .0728 | .2728 |
| $V_F/V_o$ | 1.29 | 3.13 | 1.10 |
| $Q_E$, acfm/barrel | 79 | 212 | 57 | where
$V_F$ = volume of foam in the separator,
$V_o$ = volume of oil in the separator, and
$Q_E$ = gas evolution rate, actual cubic feet per minute of gas per barrel of oil in the separator.

Reduction of the data by the least squares method gives the following equation:

$$V_F/V_o = 0.30 + 0.0133 Q_E$$

This equation can be used to determine foam and oil volumes at various separator operating conditions such as oil rate to the separator and/or the retention time of oil in the separator which is related to the oil level.

Having thus described our invention, it will be understood that such description has been given by way of illustration and example, and not by way of limitation, reference being had to the appended claims for that purpose.

What is claimed is:

1. A method for measuring the foaming characteristics of a gaseous crude oil well stream comprising:
   (a) flowing the well stream from the well at a predetermined pressure and introducing said well stream at a controlled flow rate into one end of a separator comprising an elongated horizontal vessel, said separator maintained at a controlled pressure lower than the crude oil well stream pressure so that the crude oil separates into a gaseous portion that passes to the upper portion of the separator, a body of liquid oil that extends along the bottom of the separator and a layer of foam that accumulates on top of the body of oil;
   (b) measuring the temperature of said crude oil entering said separator;
   (c) withdrawing gas from the upper portion of said separator near the end opposite the crude oil inlet and measuring the flow rate and pressure of said gaseous stream;
   (d) withdrawing oil from the bottom portion of said separator opposite the crude oil inlet and measuring the flow rate of said crude oil stream;
   (e) controlling the liquid level of crude oil within said separator;
   (f) measuring the volume of oil in said separator; and
   (g) measuring the volume of foam in said separator.

2. The method of claim 1 wherein the pressure within said separator is controlled within the range of 75 to 300 psi.

3. The method of claim 1 wherein the wellhead pressure is within the range of 100 to 700 psi.

4. The method of claim 1 wherein the volume of oil and foam in said separator are visually determined by means of a glass window provided in the end of the separator opposite the oil inlet.

5. The method of claim 1 wherein the volume of oil is determined by a liquid level gauge vertically mounted on the outside of the separator.

6. The method of claim 1 wherein the foam volume is determined by means of at least one probe extending into the upper portion of the separator.

7. A system for measuring the foaming characteristics of a gaseous crude oil well stream flowing in a production line, comprising:
   (a) an elongated horizontal separator;
   (b) a crude oil inlet into one end of said separator;
   (c) a crude oil flow conduit connecting the crude oil inlet with the crude oil production line near the wellhead;
   (d) means for controlling the flow rate of said crude oil stream being delivered to said separator;
   (e) means for measuring the temperature of said crude oil stream entering said separator;
   (f) an oil outlet line opening from the lower portion of said separator near the end opposite the crude oil inlet;
   (g) an oil flow conduit connecting said oil outlet line with said well stream production line downstream of said crude oil flow conduit connecting said oil inlet of the separator with said crude oil production line;
   (h) means for measuring the total rate of flow of said oil in said oil flow conduit;
   (i) means for controlling the liquid level of oil in said separator;
   (j) a gas outlet line opening from the upper portion of said separator near the end opposite the crude oil inlet;
   (k) a gas flow conduit connecting said gas outlet line with said oil flow conduit flowing oil from the separator;
   (l) back pressure control means in the gas outlet line for controlling the pressure in the separator to a predetermined level lower than the pressure of the crude oil well stream;
   (m) means for measuring the flow rate of gas in said gas flow conduit;
   (n) means for measuring the pressure of said gas in said gas flow conduit;
   (o) means for measuring the volume of oil in the separator; and
   (p) means for measuring the volume of foam in the separator.

8. The system of claim 7 wherein the means for determining the volume of oil and foam in the separator comprises a glass window provided in the end of the separator opposite the oil inlet end.

9. The system of claim 7 wherein the means for measuring the volume of oil in the separator is a liquid level gauge vertically mounted on the outside of the separator.

10. The system of claim 7 wherein the means for measuring the foam volume is at least one probe extending into the upper portion of the separator.

11. A system for measuring the foaming characteristics of a gaseous crude oil well stream flowing in a production line, comprising:
(a) an elongated horizontal separator;
(b) a crude oil stream inlet into one end of said separator;
(c) a crude oil flow conduit connecting the crude oil inlet with the crude oil production line near the well head;
(d) a bypass conduit communicating with said crude oil flow conduit and said crude oil production line downstream of said crude oil flow conduit communicating with the separator and the crude oil production line.
(e) means for controlling the flow rate of said crude oil stream being delivered to said separator located in said bypass conduit;
(f) means for measuring the temperature of said crude oil in said crude oil flow conduit;
(g) an oil outlet line opening from the lower portion of said separator near the end opposite the crude oil inlet;
(h) an oil flow conduit communicating with said oil outlet line and said bypass conduit;
(i) means for measuring the flow rate of oil in said oil flow conduit communicating with said oil outlet line;
(j) means for measuring the total rate of flow of oil in said oil flow conduit communicating with said oil outlet line;
(k) liquid level control means in the oil outlet line for controlling the liquid oil level in said separator;
(l) a gas outlet line opening from the upper portion of said separator near the end opposite the crude oil inlet;
(m) a gas flow conduit communicating with said gas outlet line and said bypass conduit;
(n) back pressure control means in the gas outlet line for controlling the pressure in the separator to a predetermined level lower than the pressure of the crude oil well stream;
(o) means for measuring the flow rate of gas in said gas flow conduit;
(p) means for measuring the pressure of said gas in said gas flow conduit;
(q) means for measuring the volume of oil in the separator; and
(r) means for measuring the volume of foam in the separator.

12. The system of claim 11 wherein the means for determining the volume of oil and foam in the separator comprises a glass window provided in the end of the separator opposite to the oil inlet.

13. The system of claim 11 wherein the means for measuring the volume of oil in the separator is a liquid level gauge vertically mounted on the outside of the separator.

14. The system of claim 11 wherein the means for measuring the foam volume is at least one probe extending into the upper portion of the separator.

15. A system for measuring the foaming characteristics of a gaseous crude oil well stream comprising:
(a) a separator comprising an elongated horizontal vessel;
(b) means for flowing a well stream from a well at a predetermined pressure and for introducing said well stream at a controlled flow rate into one end of said separator;
(c) means for maintaining said separator at a controlled pressure lower than said predetermined pressure whereby said well stream separates into a gaseous portion that passes to the upper portion of the separator, a body of liquid oil that extends along the bottom of the separator and a layer of foam that accumulates on top of the body of oil;
(d) means for measuring the temperature of said crude oil entering said separator;
(e) means for withdrawing gas from the upper portion of said separator near the end opposite the crude oil inlet and measuring the flow rate and pressure of said gaseous stream;
(f) means for withdrawing oil from the bottom portion of said separator opposite the crude oil inlet and measuring the flow rate of said crude oil stream;
(g) means for controlling the liquid level of crude oil within said separator;
(h) means for measuring the volume of oil in said separator; and
(i) means for measuring the volume of foam in said separator.

* * * * *